(12) United States Patent
Männle et al.

(10) Patent No.: US 8,586,692 B2
(45) Date of Patent: Nov. 19, 2013

(54) LIGHT PROTECTIVE ADDITIVE BASED ON ORGANIC/INORGANIC HYBRID POLYMER, METHOD FOR ITS MANUFACTURE AND USE THEREOF

(75) Inventors: Ferdinand Männle, Oslo (NO); Kaare Roger Rödseth, Gursken (NO); Huaitian Bu, Oslo (NO)

(73) Assignee: NOR-X Industry AS, Gursken (NO)

( * ) Notice: Subject to any disclaimer, the term of this patent is extended or adjusted under 35 U.S.C. 154(b) by 1191 days.

(21) Appl. No.: 12/083,585

(22) PCT Filed: Oct. 16, 2006

(86) PCT No.: PCT/NO2006/000359
§ 371 (c)(1),
(2), (4) Date: Jun. 10, 2008

(87) PCT Pub. No.: WO2007/053024
PCT Pub. Date: May 10, 2007

(65) Prior Publication Data
US 2009/0234147 A1    Sep. 17, 2009

(30) Foreign Application Priority Data
Oct. 14, 2005 (NO) .................................. 20054730

(51) Int. Cl.
*C08G 77/26* (2006.01)
(52) U.S. Cl.
USPC ............................................ 528/38; 528/26
(58) Field of Classification Search
USPC ...................................................... 528/38, 26
See application file for complete search history.

(56) References Cited

U.S. PATENT DOCUMENTS

| | | | |
|---|---|---|---|
| 2,929,829 A * | 3/1960 | Morehouse | 556/419 |
| 3,068,153 A * | 12/1962 | Morehouse | 424/59 |
| 6,399,798 B2 * | 6/2002 | Gschneidner et al. | 554/35 |
| 2004/0156933 A1 | 8/2004 | McNamara et al. | |
| 2005/0154180 A1 | 7/2005 | Hessefort et al. | |

FOREIGN PATENT DOCUMENTS

| | | |
|---|---|---|
| WO | WO 0148057 | 7/2001 |
| WO | WO 2004/094505 | 11/2004 |
| WO | WO 2005/100450 | 10/2005 |

OTHER PUBLICATIONS

Parham et al. (J.A.C.S. Dec. 1948, p. 4187-4189).*
David Tirrell, et al., "Polymers with Ultraviolet Absorbers as Functional Groups", 1978, Polym. Drugs, (Proc. Int. Symp.), Meeting Date 1977, pp. 542-546.
David A. Tirrell, "Preparation of Polymeric Ultraviolet Stabilizers", ACS Symposium Series (1981), 151 (Photodegradation Photostab. Coat.), pp. 43-49.
Arnaldo T. Soltermann, et al., "Phenolic-type stabilizers as generators and quenchers of singlet molecular oxygen (O2(1Deltag). Part I: methyl salicylate, salicylic acid and some related compounds", Polymer Degradation and Stability, 1995, vol. 49, pp. 371-378.

* cited by examiner

*Primary Examiner* — Kuo-Liang Peng
(74) *Attorney, Agent, or Firm* — Ladas & Parry, LLP

(57) ABSTRACT

Light protective additive based on a polybranched organic/inorganic hybrid polymer manufactured by a sol-gel process and method for its manufacture, having a chemical structure:

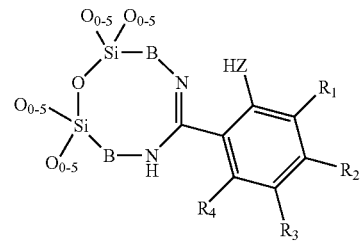

$R_1$-$R_4$ may be hydrogen, unsubstituted saturated or unsaturated $C_1$-$C_{24}$ alkyl, substituted saturated or unsaturated alkyl, substituted or unsubstituted aryl, halogen, hydroxyl, substituted or unsubstituted amine, aliphatic or aromatic carbonyl, or where $R_1$-$R_4$ are chosen among the condensation products or addition products of one or more types of chemical compositions such as acids, alcohols, phenols, amines, aldehydes, or epoxides.

8 Claims, No Drawings

LIGHT PROTECTIVE ADDITIVE BASED ON ORGANIC/INORGANIC HYBRID POLYMER, METHOD FOR ITS MANUFACTURE AND USE THEREOF

This application is a 371 of PCT/NO2006/000359 filed on Oct. 16, 2006, which claims priority to Norwegian patent application number 2005-4730, filed Oct. 14, 2005, which is incorporated herein by reference.

The present invention concerns a light protective additive based in organic/inorganic hybrid polymer and compositions that comprise such light protective additives.

BACKGROUND

Degradation processes of organic materials are typically based on oxidative degradation and may lead to discoloration (yellowing) or change of mechanical properties such as brittleness or loss of strength. Another consequence of oxidative degradation can be release of undesired low molecular weight compounds which may involve unpleasant odour or reduced aesthetics. Oxidative degradation typically limits the applicability of otherwise suitable materials or compositions. Particularly within the materials industry there is a strong need for materials that does not deteriorate significantly during their lifetime. A colour change of a product during the first few year of utilization is usually not acceptable to the customer. Examples of such products are coatings used for boats and high quality furniture.

Light protective additives are added to organic compounds to inhibit their degradation under influence of light. An extensive overview of light protective additives for polymer materials are provided by Hans Zweifel (ed.), "Plastic additives handbook", Hanser, München, 2000. As light protective additives are typically used additives with UV absorbing properties (Hans Zweifel (ed.), "Plastic additives handbook").

UV absorbers that are used in polymer materials should fulfil three important criteria. Firstly the UV absorber should have a sufficiently good absorption in the wavelength range 300-400 nm. Secondly the UV absorber should have a sufficient stability in the relevant application to avoid that its UV absorption decreases over time. Thirdly the UV absorber should be easy to mix into the material or composition in which it is to be used.

Examples of UV absorbers with good absorption in the 300-400 nm wavelength range having good stability during time of use are chemical compounds based on triphenyl triazine which is described e.g. in WO 97/36880, EP 434 608, EP 520, 938, U.S. Pat. No. 4,619,956, EP 483,488, EP 500, 496, EP 502,816, and EP 506,615. Other examples of UV absorbers with good absorption in the wavelength range 300-400 nm which also have good stability under time of use are chemical compounds based on benzo triazoles which are described e.g. in U.S. Pat. No. 5,977,219, U.S. Pat. No. 5,607, 987, and U.S. Pat. No. 5,516,914. To be able to mix such UV absorbers into polymers and polymer forming compositions such as thermoplastics, thermosetting plastics and coating forming compositions usually a step of formulation is required.

One way of avoiding such a formulation step is to chemically bond UV absorbing chemical compounds to organic polymer molecules with a branched structure. Such polymers can due to their branched structure easily be combined with all kinds of polymers and particularly with thermosetting plastics and coating forming compositions.

In addition to pure polymer materials there has also been developed products based on materials that may be described as hybrids between inorganic and organic materials, which means that these materials are macro molecules that may have an inorganic core and organic branches.

Organic polymer molecules with branched structures have an enormous economical growth potential, particularly as components in new materials. So-called dendrimers are important examples of such polymer molecules with a perfectly branched structure as well as hyperbranched polymers with statistically progressive branching. Both dendrimers and hyperbranched polymers are denoted dendritic polymers. Dendritic (from Greec: "dendron"=tree) characterizes the principle of a progressive branching that is more or less perfect (G. R. Newkome, C. N. Moorefield, F. Vögtle, "Dendrimers and Dendrons: Concepts, Syntheses, Applications", Wiley-VCH, Weinheim, (2001)). Formula 1 illustrates the principle difference between linear polymers and dendritic polymers (hyperbranched polymers and dendrimers).

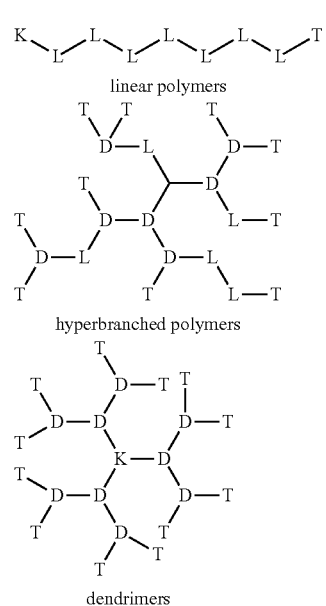

Formula 1

K = germ (the beginning of the polymer molecule
L = linear propagation
D = dendritic branching
T = termination (the end of the polymer molecule)

Dendritic polymers are particularly interesting because the T units may carry functional groups and the density of available functional groups per weight or volume unit of the polymer is much higher than what is the case for linear polymers. Functional T groups may be used to impart a function in a material, like an antioxidant, an UV absorber, or a radical scavenger as described in WO publication No. 02092668.

Alternatively the T groups may be used as very efficient cross-linkers of organic materials like epoxy resins or polyurethanes or as cross-linkers for thermoplastics. Due to the high degree of cross-linking between dendritic polymers and such organic compounds the dendritic polymers are superior cross-linkers compared to conventional cross-linkers like polyamines, polyalcohols, or multifunctional acrylates. Higher degree of cross-linking of an organic material like a cross-linked thermoplastic improves properties such as chemical resistance, weather resistance and wears resistance and makes the material useful for applications at higher temperature. (Hans Zweifel (ed.), Plastics Additives Handbook, Carl Hanser Verlag, München, (2001), 725-811). The T groups may also be used to organize the dendritic polymers in a network. As component in a material the dendritic polymer thus may induce improved barrier properties. Alternatively such dendritic polymers may be used as a binder or as a component in a thermoset plastic.

Another way of manufacturing hyperbranched polymers involves the utilization of a reactive monomer that also carries an initiator, a so-called "inimer". One example is the base catalyzed reaction between the inimer glycidol and the germ trimethylol propane as illustrated by Formula 2.

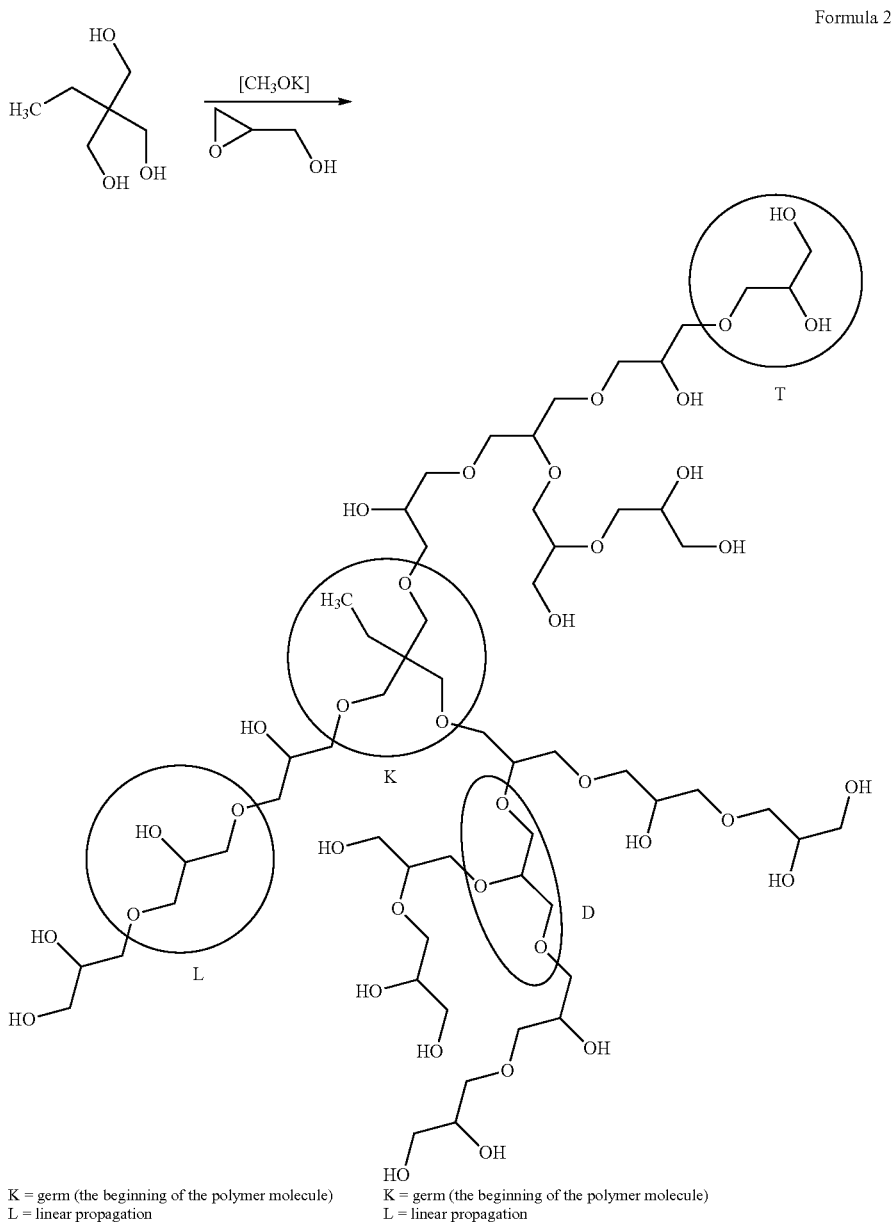

Formula 2

K = germ (the beginning of the polymer molecule)
L = linear propagation

K = germ (the beginning of the polymer molecule)
L = linear propagation

Dendrimers are usually manufactured in relatively complicated and expensive synthesis comprising several steps. The process conditions must be maintained very accurately in order to achieve a perfect progressive branch structure. Their industrial applications are therefore limited.

A general way of manufacture of hyper branched polymers was early described by Flory (P. J. Flory, Principles of Polymer Chemistry, Cornell University, (1953)). The polymerization of an $AB_2$ monomer where A may react with B but where the reactions between A and A and between B and B are precluded, leads to a hyperbranched polymer.

Hyperbranched polymers made in this way have properties that are quite similar to corresponding dendrimers (A. Sunder, R. Hanselmann, H. Frey, R. Mühlhaupt; *Macromolecules*, (1998), 32, 4240). This implies a much lower viscosity than that of linear polymers with a comparable number of free available HO-groups. A characteristic feature in the manufacturing process is that the inimer glycidol must be added very slowly to the germ and in a very thin dilution. Thus, the cost-efficiency of the process is severely reduced which is why the utility of hyperbranched polymers in industrial applications is quite limited.

It is previously known to perform certain modifications of the T groups of hyperbranched polymers. J.-P. Majoral, A.-M. Caminade and R. Kraemer, *Anales de Quimica Int Ed.*, (1997), 93, 415-421 describe the functionalizing of dendrimers containing phosphorus. The functionalizing of the T groups can be made with identical/similar chemical groups or with different chemical groups.

FR 2761691 discusses dendrimers with functional groups at the surface that are modified through a reaction with cyclic thio esters. The reaction leads to a dendrimer surface with thiol groups that are attached to the dendrimer by amide or amine bondings. The products are useful as antioxidants. The dendrimers described are of the type polyamidoamine dendrimers (PAMAM dendrimers). PAMAM dendrimers contain tertiary amines that comparatively easy may be degraded after conversion to quaternary ammonium salts or aminoxides (A. W. Hofmann, *Justus Liebigs Ann. Chem.* (1851), 78, 253-286; A. C. Cope, E. R. Trumbull, *Org. React.* (1960), 11, 317-493; A. C. Cope, T. T. Foster, p. H. Towle, *J. Am. Chem. Soc.* (1949), 71, 3929-3935). Quaternary ammonium salts or aminoxides from amine based dendrimers can be formed when additives of amine based dendrimers are incorporated/compounded into thermoplastics with subsequent processing of the thermoplastics (e.g. film blowing, extrusion, casting). Such a degradation on one hand leads to a partial deterioration of the dendrimer core and on the other hand to formation of degradation products which may leak out and thereby reduce the surface quality of the polymer product. In addition tertiary amines may during processing of the thermoplastic form free radicals by decomposition of hydro peroxides (A. V. Tobolsky, R. B. Mesrobian, *Organic Peroxides*, (1954), Interscience Publishers, New York, p. 104-106). Dendrimers and hyperbranched polymers that contain tertiary amines thereby may induce an unintended degradation of thermoplastics during their processing, storage or use.

WO 01/48057 discusses multifunctional stabilizers against thermal oxidative degradation based on a core structure containing tertiary amines. As mentioned above, this may lead to an unintended degradation of the core structure during processing, storage or use of (the) thermoplastics. The molar weight of a typical stabilizer manufactured in accordance with WO 01/48057 is 1246 g/mole.

WO 97/19987 discusses combinations of polymer additives and modified dendrimers that are useful in polymer materials. In the exemplification of WO 97/199987 the dendrimers are based on polypropylene imine (PPI) of $3^{rd}$, $4^{th}$ and $5^{th}$ generation thereby including 16, 32, and 64 terminal amine groups. The core structure contains tertiary amines which may lead to an unintended degradation of the core structure during processing, storage or use of thermoplastics. The modification of the PPI dendrimer with a fatty acid to form a multifunctional fatty acid amide may bee conducted by means of heating in a suitable solvent. The tertiary amine groups in the core structure of the dendrimer and primary amine groups at the dendrimer surface may in presence of oxygen contribute to partial degradation of the dendrimer structure. As explained above free radicals may be formed by decomposition of hydro peroxides. Such a partial degradation is indicated by a faint brown or yellow colour of the modified PPI dendrimer, like in examples 1, XI, and XII in WO 97/19987. Typical molecule weights for modified PPI dendrimers in WO 97/19987 are in the range 10 000 to 40 000 g/mole. In WO 02/092668 permanent or surface activated hyperbranched or dendritic stabilizers comprising at least one additive group and a hyperbranched or dendritic core are discussed. In the exemplification of WO 02/092668 only dendritic cores based on 2,2-bis-(hydroxymethyl)-propionic acid is used. The dendritic core and the bonding to the additive group thereby are mainly based on ester bondings, which make the stabilizer sensitive to hydrolysis. In addition the exemplification of WO 02/092668 shows that the molecules of the prepared stabilizers as determined by gel permeation chromatography is between 1000 and 1500 grams/mole. When the stabilizer shall function as an UV absorber the additive group which chemically bonds to a hyperbranched or dendritic core, is always as such approximately as good an UV absorber as the manufactured stabilizer. The way in which the additive group bonds to a hyperbranched or dendritic core has little or no influence on the UV absorbing properties of the manufactured stabilizer.

One type of particulate polymers with properties corresponding to the properties of hyperbranched polymers comprises an inorganic $Si_xO_{(1.5)x}$-core with one T group per Si atom and is known as POSS (polyhedral oligosilesquioxanes). The most common compound of this class is a POSS with x=8 and substantially cubic structure (C. Sanchez, G. J. de A. A. Soler-Illia, F. Ribot, T. Lalot, C. R. Mayer, V. Cabuil; *Chem. Mater.*, (2001), 13, 3066). The manufacture of POSS is expensive (M. C. Gravel, C. Zhang, M. Dinderman, R. M. Laine; *Appl. Organometal. Chem.*, (1999), 13, 329-336 and WO 01/10871) and their industrial applicability is therefore limited.

Another type of particulate polymers with properties corresponding to the properties of hyper-branched polymers consists of an inorganic $Si_xO_{(1.5)x}$ core that carries one T group per Si atom and may be manufactured in a sol-gel process through controlled hydrolysis and condensation of a silane with a structure:

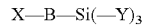

where Y is chosen among hydrolysable residues and X—B basically corresponds to the T group. The process is described e.g. in WO publication No. 0208343. Sol-gel processes may be cost efficient so that they may be conducted in industrial scale from favourable raw materials and under mild conditions, i.e. without use of high pressures or high temperatures and without particular precautions like extreme dilution or the like. Thus particulate polymers with properties corresponding to properties of hyperbranched polymers manufactured by sol gel processes are industrially applicable in many areas. Many examples of utilization of sol gel products in polymer products are known (DE 199 33 098, EP 666 290). Normally the main focus is placed upon the inorganic $Si_xO_{(1.5)x}$ core with a size in the nanometre range and thereby upon the sol-gel product as inorganic nano particle, cf. DE 199 33 098 and EP 486 469. The inorganic residues X—B are typically used to anchor the sol gel products in an organic matrix, cf. EP 486 469.

The sol gel process involving hydrolysis and condensation of a silane in which the X—B group contains one or more amide groups is particularly simple because no external catalyst is needed and because the process may be conducted at ambient temperature or under moderate heating. One example is controlled hydrolysis and condensation of γ-aminopropyl trialkoxysilane as described in applicant's own patent application, WO publication No. 0208343. Controlled hydrolysis and condensation of silanes in which the X—B group contains one or more amide groups typically leads to a sol in which the resulting particulate polymer product has an organic/inorganic structure (hybrid polymer) that is comparable with a hyperbranched polymer product with a number of more or less free amine groups in the T groups. Such organic/inorganic hybrid polymers exhibits a large number of functional T groups compared to their weight and/or volume. At the same time its compact structure compared to the structure of linear polymers ensures desirable properties like low viscosity and good admixing properties with thermoset plastics and thermoplastics. An example of an organic/inorganic hybrid polymer with properties corresponding to a hyperbranched polymer is shown by Formula 3:

Formula 3

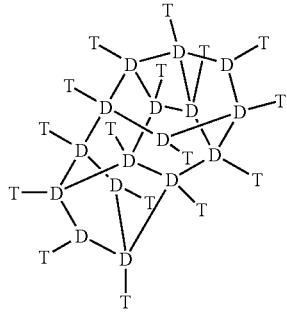

D = dendritic branching based on $SiO_{1.5}$
T = termination (functional T-groups)
D-groups that are bonded to fewer than three D units do not carry hydrolysed and/or condensed substituents Organic/inorganic hybrid polymers with properties corresponding to those of hyperbranched polymers find use e.g. as additives for thermoset plastics, in lacquers and other types of coatings for surface protection. Used in appropriate amount and particle size such hybrid polymers can contribute to a substantial improvement of the properties of the plastic material, lacquer or other type of product in question, hereunder particularly increased wear resistance/scratch resistance and/or weather resistance.

Prior art technology in the area of sol-gel processes can coarsely be divided into four main categories as explained in further detail below with reference to some examples or publications.

A first category concerns modification of non-hydrolyzed amine containing silanes (DE 2023968, WO 03/029361, EP 0253770, EP 666290) typically with bifunctional epoxy compounds (like e.g. JP 2001192485), and use thereof n coatings. Hydrolysis and condensation are thereafter conducted in some embodiments prior to the addition to the thermoplastics or coating in question. In general this method involves an undefined molecular size distribution with a high number of large molecules. This means i.a. that subsequent hydrolysis is not easily conducted since water does not easily reach all sites on the large molecules. A low degree of hydrolysis implies lower scratch resistance and weather resistance for the product. A further disadvantage is that water used for hydrolysis in presence of the organic parts of the molecules may react in an undesired manner with active groups on the organic parts. The utilization of a non-hydrolyzed alkoxy silane compound in a thermoplastic or thermoset plastic material leads to formation of alcohols such as ethanol and/or methanol during the subsequent sow hydrolysis of the silane compound, i.e. after that the thermoplastic or thermoset plastic has been exposed to moisture. This can lead to weakened mechanical properties for the thermoplastic or coating. In addition the formation of alcohols such as ethanol and/or methanol may cause migration of additives and/or degradation to the surface of a thermoplastic material or coating which can significantly reduce the surface quality.

Another category of prior art methods concerns modification of nitrogen containing sol-gel products through chemical reactions where the amine groups are not directly involved (S. kar, P. Joly, M. Granier, O. Melnyk, J.-O. Durand, *Eur. J. Org. Chem.*; (2003), 4132-4139) or are not significant (U.S. Pat. No. 5,744,243). The latter patent concerns a coating composition which is obtained by combination of a) acid catalyzed hydrolysis and condensation of silane and monomer, b) a polymerized solution of organic polymer comprising functions which are compatible with the silane monomer. The coating is used for light reflection.

A third category concerns surface modification solely of $SiO_2$ particles, i.e. silica particles which may or may not be manufactured by a sol-gel process. A (non-hydrolyzed) silane is typically used to modify these particles, the silanes thereby forming branches on the particles. This type of modification does not involve amine groups as reactive sites for the modification. The patent application No. 9603174-5 describes aqueous dispersions of silica particles in different polymers, used i.a. to increase hardness.

WO publications Nos. 9407948 and 00/22039 concern this known technology in which a surface modification of the oxide particles is conducted trough silanization. In some cases the oxide particles can be made of hydrolysed silane. These particles are used as fillers and for modification of polymers and foils. A disadvantage of products including such particles is that they are not fusible after curing and their use as hyperbranched polymers is therefore limited. A disadvantage of this technology is that each silane has several functional groups which do not necessarily bind to one and the same particle. If or when a silane binds to two different particles it contributes to an undesired agglomeration of particles. This may take place at once or over time which means that the system is unstable. It should furthermore be noted that due to the size of the silanes only a limited number of functions can be attached to each particle, i.e. the degree of hyperbranching is comparatively low. EP 0786499 describes a composition that is curable with moisture and comprises a) a multifunctional acrylate, b) at least one alkoxy-functional organometallic component (TEOS) or hydroxylate, and c) at least one trialkoxyaminosilane.

A fourth category of prior art technology is constituted by sol-gel processes based on hydrolysed silane and involving a modification with an organic monomer, prepolymer or polymer.

EP 486 469 describes an organic/inorganic hybrid polymer obtained by polymerizing an organic monomer in presence of a wholly or partially hydrolysed silane based sol. A typical example from EP 486 469 is polymerizing of methylmetacrylate in presence of a sol made using methacryl oxypropyltrimethoxysilane. The resulting composition is intended to be used for wear resistant coatings.

U.S. Pat. No. 5,674,941 teaches a coating forming composition comprising hydrolysate/condensate of a) en epoxide containing silane, b) an organic aminofunctional silane, c) a copolymer of two components chosen among an acrylate monomer, an epoxy monomer, an organosilane and/or a terpolymere of said three components, and d) a curing catalyst, e) a multifunctional acrylate, f) an initiator for radical polymerisation. This composition is very complex and a chemical conversion of amine groups to form a polybranched organic/inorganic hybrid polymer is not described.

U.S. Pat. No. 5,096,942 concerns a process in which a polymer is first made based on a hydrolysed silane, a so-called inorganic core, which is attached to a polymer chain like e.g. polystyrene. The hydrolysis of the silane is conducted so that the condensation between Si—OH groups is actually prevented. A hydrolysed metal oxide or silane is thereafter added to the hydrolysed silane resulting in an organic/inorganic hybrid polymer with properties corresponding to the properties of a hyperbranched polymer with a molecular weight in the range 1000-100000 g/mol. The silane is not nitrogen containing and no intended chemical conversion of free amine groups in the sol is mentioned in U.S. Pat. No. 5,096,942.

U.S. Pat. No. 5,110,863 teaches the manufacture of a sol containing an organosilane (with imidazol) and metal oxide which is hydrolysed and can produce an independent coating.

WO 2005 100450 concerns a method for the manufacture of different types of polybranched inorganic/organic hybrid polymers. The method is based on a chemical reaction between one amine group n a polybranched inorganic/organic hybrid polymer and a suitable monofunctional chemical compound. The reaction of two or more amine groups in a polybranched inorganic/organic hybrid polymer with a multifunctional chemical compound leads to loss of the particulate properties of the polybranched inorganic/organic hybrid polymer. Manufacture of polybranched inorganic/organic hybrid polymers with UV absorbing properties is not discussed.

Silicone based polymers and oligomers with chemical bonds to UV absorbing groups are described in JP 07267842, US 2005249690, JP 2006225358 and EP 138590.

EP 275719, EP 955288, US 2005180933 and WO 2005025491 all describe UV absorbing materials made by chemical conversion of amines and polymer amine compounds with UV absorbing chemical compounds. The UV absorption is usually strong at wavelengths<350 nm and usually strong in the wavelength range 350400 nm. These UV absorbing materials thus have a limited use as light protective material for the entire wavelength range 300-400 nm.

UV absorbers with low tendency of leakage and so-called "blooming" from materials and compositions in which they are used, are described in US 2005023268, DE 19649191, JP 10212469, and EP 744632. Leakage and blooming are reduced by improvement of the fat solubility of the UV absorber or by chemically to bind the UV absorber to a material or component in a material composition.

UV absorbers to be used in aqueous formulations are described in DE 20 2006 007 976 U1 and FR 030 4650.

OBJECTIVE

It is an object of the present invention to provide a method for the manufacture of light protective additives based on particulate, polybranched inorganic/organic hybrid polymers which can easily be mixed into polymers and polymer forming compositions such as thermoplastics, thermoset plastics and coating forming compositions without specific formulation steps.

It is a further object to provide a method as defined above in which the light protective additive has a good absorption in the wavelength range 300-400 nm.

It is still further an object to provide a method as defined above where the light protective additive has a good absorption in the wavelength range 300-400 nm and where—in addition to UV absorbing groups—other groups having light protective properties are bonded to the polybranched inorganic/organic hybrid polymer.

The Invention

The above mentioned objectives are achieved in the form of a method for the manufacture of a polybranched organic/inorganic hybrid polymer as defined by claim 1.

According to another aspect the invention provides a light protective additive as defined by claim 9.

According to further aspects the invention provides different uses of the light protective additive as defined by the claims 11, 16, 17, 18 and 19.

According to still another aspect the invention provides a thermoplastic material as defined by claim 20.

According to still another aspect the invention provides products of thermoplastic materials as defined by claims 21, 23, 25, 27 and 29.

Preferred embodiments of the invention are disclosed by the dependent claims.

A skilled artisan will understand that the group X—B is chosen so that it will not be hydrolysable at the conditions relevant for the method according to the present invention.

With "group with proton donating ability" as used herein is meant groups with ability to dissociate to a proton and a corresponding anion. Such groups include but are not limited to —H, —NH$_2$, substituted —NH$_2$, —SH.

The free amine groups are modified by a suitable chemical reaction subsequent to the completed hydrolysis and condensation of the silane. Suitable chemical reactions are conducted between the free amine groups in the T groups and reactive compounds which preferably react quantitatively with more or less free amine groups at temperatures below 470 K and pressures typically below 0.3 MPa.

Of particular interest are sol-gel processes in which the T groups can chemically be modified in one or more subsequent steps when the hydrolysis and condensation has been completed and using the same reactor equipment as used for the hydrolysis and condensation of the silane. Such batch processes form the foundation for a very cost-efficient manufacture of particulate organic/inorganic polybranched polymers which can include a high number of different T-groups and which therefore is useful in a high number of different industrial applications.

With "reactions typical of primary and secondary amines" is meant addition reactions, substitution reactions and combinations of such reactions with suitable reactants such as but not limited to compounds comprising epoxy groups, isocyanate groups, reactive double bonds, substitutable groups and proton donating groups.

With "controlled hydrolysis and condensation" as used herein is meant hydrolysis and condensation with a suitable silane compound.

The first step is hydrolysis of a suitable silane compound, R'—Si(OR)$_n$, in which the R' group does not participate in the hydrolysis or condensation reactions. Alkoxide ligands are substituted by hydroxyl groups:

Si—OR+H—OH Si—OH+ROH

A controlled amount of water and a controlled amount of glycolic solvent are added during this step. The reaction temperature and reaction time are also controlled.

The second step is condensation in which the hydroxyl groups can react with hydroxyl or alkoxy groups from other silicon centres and form Si—O—Si bonds and water or alcohol respectively.

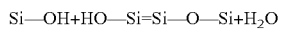

Si—OH+HO—Si=Si—O—Si+H$_2$O or

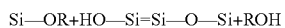

Si—OR+HO—Si=Si—O—Si+ROH

To manufacture particles with desired particle size it is required to establish chemical conditions that ensure a correct balance between the kinetics of the two reactions, condensation and hydrolysis. While the condensation contributes to formation of polymer chains from (individual) monomers the hydrolysis contributes to a polycrystalline precipitation or oxohydroxide precipitation. The combination of aminofunctional silanes and exchange of alkoxide groups with strong ligands will slow the hydrolysis reaction compared to the condensation reaction, which ensures that the mentioned polymer chains do not become too long but remain within the size of oligoomers. In practice this means that the particles typically will be only a few nanometers in size, more typically less than 10 nm. A suitable stabilizer is typically added to the reaction composition to avoid oxidative degradation of reactant and reaction products during hydrolysis and condensation and subsequent modification. The resulting solution comprises inorganic polymer particles dispersed in a solvent.

CLOSER DESCRIPTION OF THE INVENTION/PREFERRED EMBODIMENTS

In preferred embodiments of the method according to the invention, the aromatic carboxyl acid derivative is chosen among:

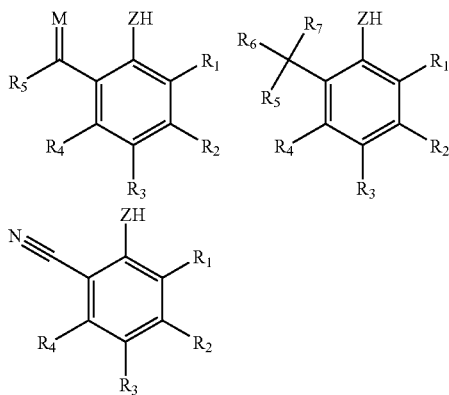

where $R_1$-$R_4$ are chosen among groups such as hydrogen, unsubstituted saturated or unsaturated $C_1$-$C_{24}$-alkyl, substituted saturated or unsaturated $C_1$-$C_{24}$-alkyl, substituted or unsubstituted aryl, halogen, hydroxyl, substituted or unsubstituted amine, aliphatic or aromatic carbonyl, while one or more carbon atoms in the carbon chains of said compounds can be substituted by one or more element chosen among oxygen, nitrogen, sulphur, phosphorus, silicon, and boron, or where $R_1$-$R_4$ are chosen among the condensation products or addition products of one or more types of chemical compositions such as acids, alcohols, phenols, amines, aldehydes, or epoxides and where $R_1$-$R_4$ can form substituted or unsubstituted aromatic ring structures that together with the existing aromatic ring form a larger ring structure than phenyl, while M, Z are chosen among O, N, S and where $R_5$-$R_7$ are chosen among R1-O, $R_1R_2N$ or $R_1$—S.

It is furthermore preferred that the carboxylic acid or carboxylic acid derivative is chosen so that the polybranched organic/inorganic hybrid polymer which is suitable as a light protective additive is water dispergable.

It is furthermore possible and in some situations preferred that two or more of R1-R4 are chosen in a manner with respect to size, shape and structure so they can contribute to an extension of the aromatic structure to an aromatic structure with more than 6π electrons. An example is 2-hydroxy-1-naphtylic acid [2283-08-1] which has 10π electrons in relation to 2-hydroxybenzoic acid (salicylic acid) [6972-7] which has 6π electrons.

In a preferred embodiment the method according to the present invention provides a sol-gel process comprising at least two steps in a defined chronology, so that:

i) in the first step the core is prepared by controlled hydrolysis and condensation of a silane with structure:

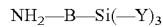

Where B is a lineage group chosen among saturated or unsaturated $C_1$-$C_{18}$ alkylene, substituted or unsubstituted arylene, the carbon chains of said compounds possibly containing one or more branches and one or more of the carbon atoms may be substituted by the elements oxygen, nitrogen, sulphur, phosphorous, silicon, and boron while Y is a hydrolysable group, while ii) in at least one subsequent step the UV absorbing organic branches are developed by reacting two —B—$NH_2$ groups with a carboxylic acid or carboxylic acid derivative comprising one of the following chemical structures:

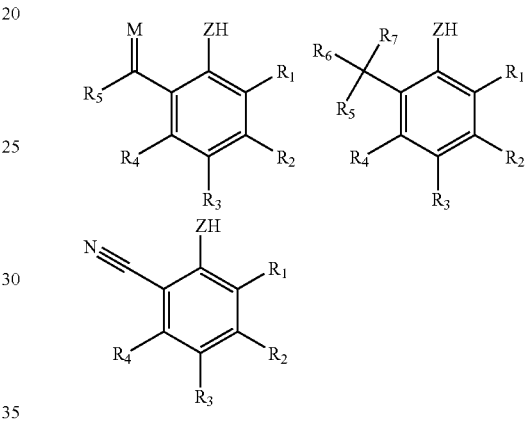

where $R_1$-$R_4$ are chosen among groups like hydrogen, unsubstituted saturated or unsaturated $C_1$-$C_{24}$ alkyl, substituted saturated or unsaturated $C_1$-$C_{24}$ alkyl, substituted or unsubstituted aryl, halogen, hydroxyl, substituted or unsubstituted amine, aliphatic or aromatic carbonyl, while one or more of the carbon atoms in said chains may be substituted by the elements oxygen, nitrogen, sulphur, phosphorus, silicon, and boron, or where $R_1$-$R_4$ are chosen among condensation products or addition products of one or more types of chemical compounds such as acids, alcohols, phenols, amines, aldehydes, or epoxides and where $R_1$-$R_4$ can form substituted or unsubstituted aromatic ring structures that together with the existing aromatic ring form a larger aromatic ring structure than phenyl, where M, Z are chosen among O, N, S and where $R_5$-$R_7$ are chosen among $R_1$—O, $R_1R_2N$ or $R_1$—S.

In the method according to the invention some —B—$NH_2$ groups may react in pairs with a carboxylic acid or a carboxylic acid derivative while the remaining —B—$NH_2$ groups wholly or partially react individually with carboxylic acids or carboxylic acid derivatives.

In some embodiments of the method of the invention, which can also be preferred, the —B—$NH_2$ groups are only partially reacted chemically with a carboxylic acid or a carboxylic acid derivative while the rest —B—$NH_2$ groups react wholly or partially in per se known addition or substitution reactions to bind at least one type of stabilizer to the polybranched particulate organic/inorganic hybrid polymer and that in such reactions reactive compounds are used including but not limited to epoxides, cyclic and non-cyclic acid derivatives, blocked and non-blocked isocyanates, compounds with reactive double bonds, aldehydes, ketones, and proton donating compounds comprising or attached to suitable stabilizers and stabilizing groups, including, but not limited to, antioxidants and/or radical scavengers, including but not limited to, phenols, 2,6-substituted phenols, compounds containing 2,6, 6,6-tetramethylpiperidine and where the optional more than one —B—NH$_2$ group are attached to a certain stabilizer.

According to a particularly preferred embodiment of the invention B is propylene, Z is oxygen while R$_1$-R$_4$ are hydrogen.

The light protective additive of the present invention based on a polybranched organic/inorganic hybrid polymer that can be manufactured by a sol-gel process in which the sol-gel product wholly or partially is comprised by the chemical basic structure:

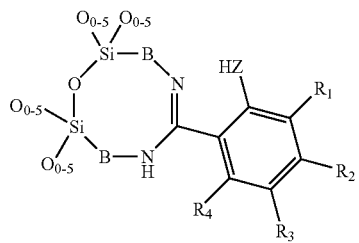

where R$_1$-R$_4$ are chosen among groups like hydrogen, unsubstituted saturated or unsaturated C$_1$-C$_{24}$ alkyl, substituted saturated or unsaturated C$_1$-C$_{24}$ alkyl, substituted or unsubstituted aryl, halogen, hydroxyl, substituted or unsubstituted amine, aliphatic or aromatic carbonyl, while one or more of the carbon atoms in said chains may be substituted by the elements oxygen, nitrogen, sulphur, phosphorus, silicon, and boron, or where R$_1$-R$_4$ are chosen among condensation products or addition products of one or more types of chemical compounds such as acids, alcohols, phenols, amines, aldehydes, or epoxides and where R$_1$-R$_4$ can form substituted or unsubstituted aromatic ring structures that together with the existing aromatic ring form a larger aromatic ring structure than phenyl, where M, Z are chosen among the elements oxygen, nitrogen, and sulphur.

It is particularly preferred that B is propylene, Z is oxygen, and R$_1$-R$_4$ all are hydrogen. The polybranched organic/inorganic hybrid polymer manufactured in accordance with claim 1 or the light protective additive as defined by claim 9 are useful as a functional additive in thermoplastics, thermoset plastics or compositions. Such use can include combinations with other functional additives, typical additives of per se known specie and type, such as antioxidants, radical scavengers, UV filters, process stabilizers, dyes.

It has been found that the thermoplastics, thermoset plastics or compositions containing the polybranched organic/inorganic hybrid polymer, exhibits less leakage of components or degradation products than corresponding thermoplastics, thermoset plastics or compositions, lacking the polybranched organic/inorganic hybrid polymer do. The components exhibiting reduced leakage are suitable as light protective additives.

Components which may leak from thermoplastics, thermoset plastics or material compositions include e.g. polymer additives such as stabilizers, radical scavengers, process facilitators and dyes.

The polybranched organic/inorganic hybrid polymer manufactured in accordance with the first aspect of the present invention or the light protective additive according to the second aspect of the present invention are useful as functional additives in polyolefins, optionally in combination with a prodegradant.

The polybranched organic/inorganic hybrid polymer manufactured in accordance with the first aspect of the invention or the light protective additive according to the second aspect of the invention are useful as a component in suntan lotions or other cosmetic products.

The polybranched organic/inorganic hybrid polymer manufactured in accordance with the first aspect of the present invention or the light protective additive according to the second aspect of the invention are useful as components in adhesive products, lacquers and coating forming products.

The polybranched organic/inorganic hybrid polymer manufactured in accordance with the first aspect of the present invention or the light protective additive according to the second aspect of the invention are useful in compositions in which water is included as a solvent or a dispersing agent.

Thermoplastic materials comprising the light protective additive according to the second aspect of the present invention or a polybranched organic/inorganic hybrid polymer manufactured in accordance with the first aspect of the invention are also parts of the present invention. So is also any product manufactured by such a thermoplastic material when processed with film blowing or foil extrusion with film or foil as end products or intermediate products, hereunder bis-oriented film. Such products typically include shopping bags, sunlight collector foils, other types of foils used for agricultural purposes, foodstuff packaging, other packaging, and other types of bags and sacks.

Included as part of the invention are also products of thermoplastics as described above and which are processed with injection moulding to injection moulded end or intermediate products. Such products typically include foodstuff packaging, other packaging, disposable articles for household or industry or for use together with foodstuff and or beverage.

Included as part of the invention are furthermore products of thermoplastics as described above and which are processed with thermoforming techniques to thermoformed end or intermediate products. Such products typically include foodstuff packaging, other packaging, disposable articles for household or industry or for use together with foodstuff and/or beverage.

Included as part of the present invention are also products of thermoplastics as described above and which are processed by means of extrusion to extruded end or intermediate products. Such products typically include products for industrial purposes, constructional purposes, hereunder transportation, building industry, fibrous products, band shaped products, hereunder woven and non-woven products.

Finally products of thermoplastic materials as mentioned above and which are processed by means of blow moulding to blow moulded end or intermediate products are included as part of the present invention. Such products typically include foodstuff packaging, other packaging, disposable articles for household or industry or for use together with foodstuff or beverage.

EXAMPLES

Experiment 1

Manufacture of a polybranched organic/inorganic hybrid polymer, suitable as a light protective additive, by a sol-gel process in a 5 litre reactor (first step of the total process).

In a t5 litre reactor (NORMAG Labor.-und Prozesstechnik, Imenau, Germany) with a temperature adjustable heat jacket, stirrer, thermometer, dropping funnel, vertical cooler with column head for rapid exchange between reflux and distillation, and vacuum connection (membrane pump), is set to 2801 grams (12.7 moles) γ-aminopropyltriethoxysilane (DYNASYLAN® AMEO, Degussa AG, Germany). A mixture of 821 grams (7.6 moles) of 2-butoxyethanol ( )DOWANOL EB, Dow Chemical, USA) and 296 grams (16.4 moles) of water and 6 grams of 2,2,6,6-tetramethylpiperidine (Adrich Norway) was added. The resulting mixture was heated with reflux for 45 minutes. Then volatile reaction products or reactants were removed by vacuum distillation at temperatures in the reaction mixture between 110° C. and 160° C. and a vacuum gradient from about 1000 mbar to less than 20 mbar. The distillation is terminated when the pressure in the round flask has reached 20 mbar or less for 10 minutes. About 2334 ml distillate was collected. The reaction product is a clear colourless liquid with Gardner Color=1 (Gardner Color Scale/ASTM D1544).

Experiment 2

Manufacture of polybranched organic/inorganic hybrid polymer suitable as light protective additive by a reaction of the intermediate product from the first step of the total process (Experiment 1) with an aromatic carboxylic acid derivative (a further step of the total process).

600 grams of diethyleneglycol monobutylether [112-34-5] was added to 600 grams of the product from Experiment 1. The mixture is heated to 70° C. Then 480 grams of methyl salicylate [119-36-8] was added and the reaction mixture was heated to 90° C. for three hours. After cooing the product is a viscous gel.

Experiment 3

Manufacture of a polybranched organic/inorganic hybrid polymer suitable as light protective additive by reaction of the intermediate product from the first step of the total process (Experiment 1) with aromatic carboxylic acid derivative (two additional steps (steps two and three) of the total process).

122 grams 3,5 di-tert-butyl-4-hydroxybenzoic acid hexadecylester [067845-93-6] is dissolved in 1000 grams of methanol. 375 grams of the product from Experiment 1 is added. The mixture is heated to 70 C. Then 181 grams of methyl salicylate is added and the reaction mixture is heated to 90 C for three hours. After cooling white crystals are formed which are washed with methanol and dried.

Experiment 4

Manufacture of a polybranched organic/inorganic hybrid polymer suitable as light protective additive by reaction of the intermediate product from the first step of the total process (Experiment 1) with an aromatic carboxylic acid derivative (step two of the total process).

18.1 grams methyl salicylate was introduced into a 500 ml three-neck round flask furnished with heat jacket, thermometer, reflex-/distillation cooler and dropping funnel. 200 grams of 2-butoxyethanol was added to the round flask and its content was heated to 120° C. 140 grams of the product from Experiment 1 was dispersed in 14.0 grams of xylene and added to the round flask trough the dropping funnel within ten minutes. The reaction mixture was stirred at 120° C. for 1 hour. Then the reaction mixture was heated to 180-200° C. and methanol and 2-butoxyethanol were distilled out. The product in the round flask was a yellow masse which set when cooled and which was completely soluble in 2-butoxyethanol.

Experiment 5

Manufacture of a polybranched organic/inorganic hybrid polymer suitable as light protective additive by reaction of the intermediate product from the first step of the total process (Experiment 1) with an aromatic carboxylic acid derivative (step two of the total process).

20.0 grams of 4-methoxy salicylic acid methyl ester was introduced into a 500 ml three-neck round flask furnished with heat jacket, thermometer, reflux-I distillation cooler and dropping funnel. 200 grams of 2-butoxyethanol was added to the round flask and its content was heated to 120° C. 14.0 grams of the product for Experiment 1 was dispersed in 14.0 grams of xylene and added to the round flask through the dropping funnel within 10 minutes. The reaction mixture was stirred at 120° C. for 1 hour. Then the reaction mixture was heated to 180-200° C. and methanol and 2-butoxyethanol were distilled out. The product in the round flask was a yellow masse which set upon cooling and which was completely soluble in 2-butoxyethanol.

Experiment 6

Manufacture of a polybranched organic/inorganic hybrid polymer suitable as light protective additive by reaction of the intermediate product from the first step of the total process (Experiment 1) with an aromatic carboxylic acid derivative (step two of the total process).

54.0 grams of methyl salicylate was introduced into a 500 ml three-neck round flask furnished with heat jacket, thermometer, reflux-/distillation cooler and dropping funnel. 120 grams of 2-butoxyethanol was added to the round flask and its content was heated to 120° C. 26.8 grams of the product from Experiment 1 was dispersed in 8.0 grams of xylene, 8.0 grams of ethanol, and 42 grams of 2-butoxyethanol and added to the round flask through the dropping funnel within 10 minutes. The reaction mixture was stirred at 120° C. for 1 hour. Then the reaction mixture was heated to 180-200° C. and methanol and 2-butoxyethanol were distilled out. Residues of volatile components were removed by vacuum distillation at 180-200° C. and 20 mbar. The product in the round flask was a yellow masse which set upon cooling into stings of about 1 mm thickness and 20 cm length.

Experiment 7

Characterization of the UV Filter Effect (UV Absorption Effect)

The UV filter effect of polybranched organic/inorganic hybrid polymer suitable as a light protective additive was characterized by measuring the total transmission in the wavelength range 300-400 nm of solutions of 8 grams of polybranched organic/inorganic hybrid polymer in 100 grams of 2-butoxyethanol. A UV-VIS spectrophotometer with diode array detector (Hewlett Packard HP 8453) was used. The solutions were measured in 10 mm quarts cuvettes. The UV-VIS spectrophotometer was reset to zero by measuring a 10 mm quarts cuvette filled with air. The UV-VIS spectrophotometer gives the transmission as a number value from 0% to 100% with a 1 nm resolution. The total transmission was calculated by adding all number values from 300400 nm. If the content in the quartz cuvette is useful as a light protective additive, the sum is a number significantly smaller than 10 000. If the content of the quartz cuvette is poorly suitable as a light protective additive the sum is a number fairly close to 10 000.

In addition to polybranched organic/inorganic hybrid polymer suitable as light protective additive, the reactants, solvents and reference materials were measured. The results are shown in table 1.

| Type | Name | Total transmission |
|---|---|---|
| Polybranched organic/inorganic hybrid polymer (starting material) | from experiment 1 | 10818 |
| Polybranched organic/inorganic hybrid polymer | from experiment 2 | 1046 |
| Polybranched organic/inorganic hybrid polymer | from experiment 3 | 1569 |
| Polybranched organic/inorganic hybrid polymer | from experiment 4 | 10 |
| Polybranched organic/inorganic hybrid polymer | from experiment 5 | 807 |
| polybranched organic/inorganic hybrid polymer | from experiment 6 | 736 |
| solvent | 2-butoxyethanol | 11023 |
| reference (starting material) | Methyl salicylate | 4780 |
| reference (starting material) | 4-methoxy salicylic acid methyl ester [2237-36-7] | 6473 |
| reference | Salicylamide (2-hydroxy-benzamide) [65-45-2] | 3712 |
| reference | Chimasorb 81 (Ciba Specialty Chemicals, Switzerland) | 3 |

The results show that polybranched organic/inorganic hybrid polymer suitable as light protective additive, can have a good UV filter effect. Polybranched organic/inorganic hybrid polymer suitable as a light protective additive manufactured in Experiment 4, exhibit a UV filter effect comparable to the commercial UV filter Chimasorb 81.

Polybranched organic/inorganic hybrid polymer suitable as light protective additive manufactured in Experiment 4 exhibits a significantly better UV filter effect than the starting materials, polybranched organic/inorganic hybrid polymer manufactured in Experiment 1 and methyl salicylate. This shows that the UV filter effect not can be explained by the UV filter effect in the starting materials. The UV filter effect is mainly formed in step two of the total process.

Polybranched organic/inorganic hybrid polymer suitable as light protective additive manufactured in Experiment 4 exhibits a significantly better UV filter effect than the reference salicylic amide. This indicates that the UV filter effect can not be explained by a conversion of the functional amino groups in the starting material polybranched organic/inorganic hybrid polymer manufactured in Experiment 1 to salicylic amide groups.

Experiment 8

Polybranched organic/inorganic hybrid polymer suitable as light protective additive manufactured in Experiment 4 by means of $^1$H-NMR spectroscopy. The NMR spectrometer was of type, Gemini 300 MHz (Varian Inc., USA). Deuterized chloroform was used as solvent The $^1$H-NMR spectre has wide resonance peaks, which is typical for the polymer compounds dissolved in chloroform. The resonance peaks are in the range 6.6 ppm-8 ppm (aromatic $^1$H resonances) and 0.5 ppm-3.4 ppm (aliphatic $^1$H resonances).

The reaction conducted in Experiment 4 can lead to following structure elements.

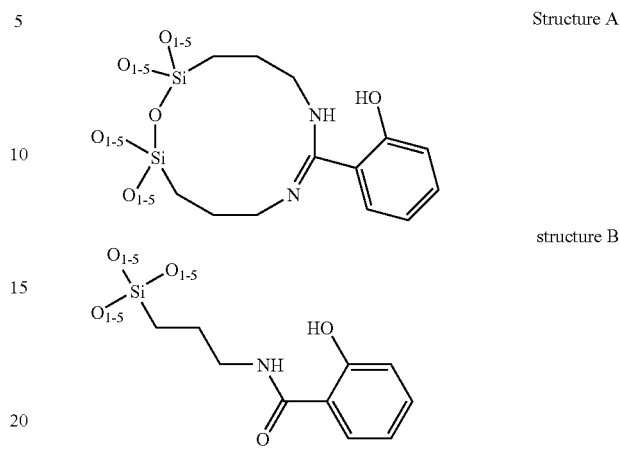

Structure A structure B

Structure B is formed by a reaction between one of the functional amino groups in the starting material polybranched organic/inorganic hybrid polymer manufactured in Experiment 1 with carboxylic ester group in methyl salicylate. Structure B can be converted to structure A if another of the functional amino groups in the starting material polybranched organic/inorganic hybrid polymer manufactured in Experiment 1 reacts with the carboxylic amide group of structure B.

The $^1$H-NMR spectres of structure A and structure B were calculated with $^1$H-NMR predictor (Advanced Chemistry Development Inc., Toronto Canada, http://www.acdlabs.com)

The aromatic $^1$H resonances in structure A lays between 6.8 ppm and 8.0 ppm. The aromatic $^1$H resonances in structure B lays between 6.8 ppm and 7.5 ppm. This shows that structure A is present in polybranched organic/inorganic hybrid polymer, suitable as light protective additive, manufactured in Experiment 4. A comparison of the areas in the aromatic $^1$H resonances and aliphatic $^1$H resonances implies that polybranched organic/inorganic hybrid polymer, suitable as light protective additive, manufactured in Experiment 4, generally is comprised by 50% of structure A and 50% of structure B. Structure A, having a chemical structure of type amidine, has a lower total transmission from 300 to 400 nm than the corresponding chemical structure of type amide, in structure B (Hans Zweifeld (ed), "Plastic additives handbook", Hanser, München, 2000). Thus the result of Experiment 7 supports the conclusion of the presence of structure A in polybranched organic/inorganic hybrid polymer suitable as light protective additive as manufactured in Experiment 4.

Experiment 9

Manufacture of a masterbatch based on polypropylene and polybranched organic/inorganic hybrid polymer suitable as light protective additive.

57.0 grams of polybranched organic/inorganic hybrid polymer suitable as light protective additive manufactured in Experiment 6, 30.8 grams Brij 76 (Aldrich Norway), 5.6 grams of masterbatch 9-9241 (Nor-X Industry AS, Norway) and 650 grams of non-stabilized polypropylene random copolymer R 305 (Nor-X Industry AS, Norway), was extruded in a double screw extruder (Clextral) at 200 C and a retention time of 60-70 seconds. The product was denoted MB 0.

MB 0 was extruded and granulated once more and the product denoted MB 1.

348 grams of MB 0 was mixed with 28 grams of the commercial light protective additive Cyasorb UV-3529 (Cytec Inc., USA). The mixture was extruded and granulated and the product denoted MB 2.

Experiment 10

Manufacture of polypropylene tension rods.

| | | |
|---|---|---|
| Tipplen K948 | polypropylene block copolymer | TVK, Hungary |
| MB 1 | masterbatch with light protective additive | Experiment 9 |
| MB 2 | masterbatch with light protective additive | Experiment 9 |
| 9-9233/ 9-9241 | masterbatch with prodegradant | Nor-X Industry AS, Norway |

Masterbatches with prodegradants like 9-9233/9-9241 contributes to rapid light induced degradation of thermoplastics (WO 2004094516, WO 2006043827).

TABLE 2

| tension rod number | Tipplen K948 | MB 1 | MB 2 | 9-9233/9-9241 |
|---|---|---|---|---|
| 60927-K948-01 | 100.00% | 0.00% | 0.00% | 0.00% |
| 60927-K948-02 | 93.75% | 6.25% | 0.00% | 0.00% |
| 60927-K948-03 | 91.75% | 6.25% | 0.00% | 2.00% |
| 60927-K948-04 | 93.75% | 0.00% | 6.25% | 0.00% |
| 60927-K948-05 | 91.75% | 0.00% | 6.25% | 2.00% |
| 60927-K948-06 | 98.00% | 0.00% | 0.00% | 2.00% |

The components of table 2 were dry blended and injection moulded test rods were manufactured according to ASTM D3641. The test rods were subsequently used for tests of tensile strength.

Experiment 11

Manufacture of polyethylene foil

| | | |
|---|---|---|
| FA6220 | LDPE (polyethylene low density) | Borealis AS, Norge |
| MB 1 | masterbatch with light protective additive | Experiment 9 |
| MB 2 | masterbatch with light protective additive | Experiment 9 |
| 9-9233/ 9-9241 | masterbatch with prodegradant | Nor-X Industry AS, Norway |

TABLE 3

| foil number | FA6220 | MB 1 | MB 2 | 9-9233/9-9241 |
|---|---|---|---|---|
| 60928-01 | 100.00% | 0.00% | 0.00% | 0.00% |
| 60928-02 | 95.00% | 5.00% | 0.00% | 0.00% |
| 60928-03 | 95.00% | 0.00% | 5.00% | 0.00% |
| 60928-04 | 93.00% | 5.00% | 0.00% | 2.00% |
| 60928-05 | 93.00% | 0.00% | 5.00% | 2.00% |
| 60928-06 | 98.00% | 0.00% | 0.00% | 2.00% |
| 60928-07 | 98.00% | 2.00% | 0.00% | 0.00% |
| 60928-08 | 96.00% | 2.00% | 0.00% | 2.00% |
| 60928-09 | 90.00% | 10.00% | 0.00% | 0.00% |
| 60928-10 | 88.00% | 10.00% | 0.00% | 2.00% |

The components of table 3 were dry blended and film was blown on a labor film blowing machine. The films had a thickness of 10-20 µm.

Experiment 12

Accelerated Ageing and Mechanical Testing of Polypropylene Test Rods

Test rods made under Experiment 10 were subjected to accelerated ageing according to ISO 4892-3 in a Atlas UVCON weather-o-meter (Atlas Inc., USA) equipped with UVA 340 fluorescence lamps. The test cycles comprised 4 hours UV radiation with dry heating to 70° C., 30 minutes of water spray at 10-12° C. and 3 hours 30 minutes of condensation at 50° C.

The test rods were tested with respect to tensile strength according to ASTM D638 at various points in time. The results of the tensile strength testing are described in the form of maximum tensile strength [MPa]. Table 4 shows the results of this test.

TABLE 4

| tension rod number | max tensile strength/ 0 hours ageing | max tensile strength/ 72 hours ageing | max tensile strength/0240 hours ageing |
|---|---|---|---|
| 60927-K948-01 | 22.76 ± 0.49 | 24.29 ± 0.72 | 12.41 ± 1.83 |
| 60927-K948-02 | 23.48 ± 0.60 | 24.10 ± 0.43 | 17.59 ± 0.92 |
| 60927-K948-03 | 22.21 ± 0.31 | 21.48 ± 0.90 | 17.51 ± 1.46 |
| 60927-K948-04 | 22.66 ± 0.46 | 23.59 ± 0.41 | 23.91 ± 0.44 |
| 60927-K948-05 | 23.22 ± 0.19 | 23.64 ± 0.36 | 23.80 ± 0.30 |
| 60927-K948-06 | 22.72 ± 0.67 | 17.57 ± 1.16 | 12.02 ± 1.36 |

The results show that polybranched organic/inorganic hybrid polymer manufactured according to the present invention is suitable as a light protective additive for thermoplastics alone or in combination with other light protective additives.

The results also show that a polybranched organic/inorganic hybrid polymer manufactured according to the present invention is suitable as a light protective additive to reduce the degradation rate of thermoplastics containing at least one prodegradant.

Experiment 13

Accelerated Ageing and Mechanical Testing of Polyethylene Foil

The films made under Experiment 11 were cut in 10 mm wide strips parallel to the foil blowing direction. The film strips were subjected to accelerated ageing according to ISO 4892-3 in an Atlas UVCON weather-o-meter (Atlas Inc., USA), equipped with UVA-340 fluorescence lamps. The test cycle comprised 4 hours of UV radiation hours with dry heating to 70° C., 30 minutes of water spray at 10-12° C. and 3 hours 30 minutes of condensation at 50° C.

The film strips were tested with respect to tensile strength at various points in time. The results of the tensile strength testing are described in the form of maximum tensile strength [MPa]. Table 5 shows the results of these tensile strength tests.

| foil number | max tensile strength/ 0 hours ageing | max tensile strength/ 0 hours ageing |
|---|---|---|
| 60928-01 | 8.64 ± 1.16 | 6.09 ± 0.45 |
| 60928-02 | 9.01 ± 3.20 | 6.78 ± 0.59 |
| 60928-03 | 10.26 ± 4.12 | 7.68 ± 3.38 |
| 60928-04 | 8.70 ± 1.01 | 4.39 ± 1.73 |
| 60928-05 | 8.78 ± 3.19 | 4.01 ± 0.72 |
| 60928-06 | 12.59 ± 6.60 | 3.18 ± 1.52 |
| 60928-07 | 6.54 ± 3.75 | 4.83 ± 1.59 |
| 60928-08 | 6.82 ± 3.83 | 4.49 ± 1.19 |
| 60928-09 | 15.13 ± 8.81 | 8.45 ± 3.48 |
| 60928-10 | 13.34 ± 6.65 | 8.47 ± 0.71 |

The results show that polybranched organic/inorganic hybrid polymer manufactured according to the invention is suitable as a light protective additive for thermoplastics alone or in combination with other light protective additives.

The results also show that a polybranched organic/inorganic hybrid polymer manufactured according to the invention is suitable as a light protective additive to reduce the degradation rate of thermoplastics containing at least one prodegradant.

Experiment 14

Water Containing Mixtures with Polybranched Organic/Inorganic Hybrid Polymer Suitable as a Light Protective Additive Drops of water were added to a 2.04 grams solution of polybranched organic/inorganic hybrid polymer suitable as light protective additive manufactured in Experiment 6 in 2-butoxyethanol (18.7% v/v). Upon addition of 1.0 grams of water a clear solution was still maintained. This solution had a total transmission of 139 measured in the manner described in Experiment 7.

This shows that polybranched organic/inorganic hybrid polymer suitable as light protective additive according to the present invention is useful as a UV absorber in aqueous combinations.

The invention claimed is:

1. Method for the manufacture of a polybranched organic/inorganic hybrid polymer suitable as a light protective additive in a total process comprising a sol-gel process in which hydrolysable metal compounds with functional amino groups are reacted in a first step comprising the formation of a core under controlled and complete hydrolysis and condensation with a silane of formula:

$$NH_2—B—Si(—Y)_3$$

where B is a linkage group chosen among saturated or unsaturated $C_1$-$C_{18}$ alkylene, substituted or unsubstituted arylene, in which the carbon chains may include one or more branches and/or that one or more carbon atom may be substituted by the elements oxygen, nitrogen, sulphur, silicon, and boron, while Y is a hydroysable residue; and wherein the total process comprises at least one additional step in which one or more of said functional amino groups are reacted with an aromatic carboxylic acid derivative comprising a group with a proton donating ability in ortho position to the carboxylic acid derivative group.

2. Method as claimed in claim 1, wherein the aromatic carboxylic acid derivative is chosen among:

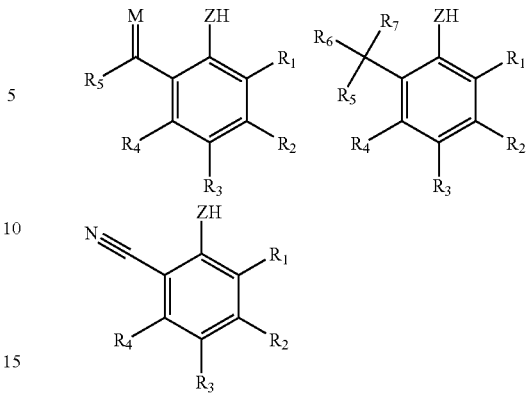

where $R_1$-$R_4$ are selected from the group consisting of hydrogen, unsubstituted saturated or unsaturated $C_1$-$C_{24}$-alkyl, substituted saturated or unsaturated $C_1$-$C_{24}$-alkyl, substituted or unsubstituted aryl, halogen, hydroxyl, substituted or unsubstituted amine, aliphatic and aromatic carbonyl, while one or more carbon atoms in the carbon chains of said compounds can be substituted by one or more elements selected from the group consisting of oxygen, nitrogen, sulphur, phosphorus, silicon, and boron, or where $R_1$-$R_4$ are chosen among the condensation products or addition products of acids, alcohols, phenols, amines, aldehydes, and epoxides, and where $R_1$-$R_4$ can form substituted or unsubstituted aromatic ring structures that, together with the existing aromatic ring, form a larger ring structure than phenyl, while M, Z are chosen among O and S, and where $R_5$-$R_7$ are chosen among $R_1$—O, $R_1R_2N$ or $R_1$—S.

3. Method as claimed in claim 2, wherein the carboxylic acid derivative is chosen so that the polybranched organic/inorganic hybrid polymer suitable as light protective additive is water dispersible.

4. Method as claimed in claim 2, wherein two or more of $R_1$-$R_4$ can contribute to extend the aromatic ring structure to a ring structure with more than 6 π-electrons.

5. Method as claimed in claim 1, wherein in the at least one subsequent step, UV absorbing branches are developed by reacting two groups B—$NH_2$ with one carboxylic acid derivative comprising one of said chemical structures:

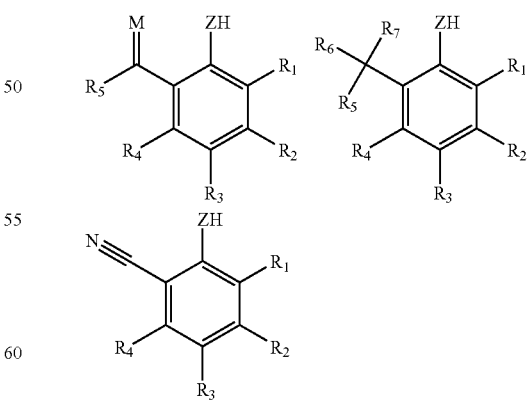

where $R_1$-$R_4$ are selected from the group consisting of hydrogen, unsubstituted saturated or unsaturated $C_1$-$C_{24}$-alkyl, substituted saturated or unsaturated $C_1$-$C_{24}$-alkyl, substituted or unsubstituted aryl, halogen, hydroxyl, substituted or unsubstituted amine, aliphatic and aromatic carbonyl, while one or more carbon atoms in the carbon chains of said compounds can be substituted by one or more elements selected from the group consisting of oxygen, nitrogen, sulphur, phosphorus, silicon, and boron, or where $R_1$-$R_4$ are chosen among the condensation products or addition products of acids, alcohols, phenols, amines, aldehydes, or epoxides and where $R_1$-$R_4$ can form substituted or unsubstituted aromatic ring structures that together with the existing aromatic ring form a larger ring structure than phenyl, while M, Z are chosen among O and S, and where $R_5$-$R_7$ are chosen among $R_1$—O, $R_1R_2N$ or $R_1$—S.

6. Method as claimed in claim 5, wherein some —B—$NH_2$ groups are reacted in pairs with carboxylic acid derivatives and that the remaining —B—$NH_2$ groups wholly or partially are reacted individually with carboxylic acids or carboxylic acid derivatives.

7. Method as claimed in claim 5, wherein the —B—$NH_2$ groups are only partially reacted so that two —B—$NH_2$ groups chemically react with a carboxylic acid derivative, and that the remaining —B—$NH_2$ groups react wholly or partially to attach at least one stabilizer to a polybranched, particulate, organic/inorganic hybrid polymer and that in such reactions, selective compounds comprising epoxides, cyclic and non-cyclic acid derivatives, blocked and unblocked isocyanates, compounds with reactive double bonds, aldehydes, ketones and proton donating compounds comprising or being attached to suitable stabilizers and stabilizing groups are used, comprising antioxidants and/or radical scavengers, comprising phenols, 2,6-substituted phenols, compounds comprising 2,2,6,6-tetramethylpiperidine and where the —B—$NH_2$ group can be attached to a certain stabilizer.

8. Method as claimed in claim 5, wherein B is propylene, Z is oxygen, $R_1$-$R_4$ are hydrogen.

* * * * *